(12) United States Patent
Friedlander et al.

(10) Patent No.: US 9,002,888 B2
(45) Date of Patent: Apr. 7, 2015

(54) MINIMIZATION OF EPIGENETIC SURPRISAL DATA OF EPIGENETIC DATA WITHIN A TIME SERIES

(75) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 105 days.

(21) Appl. No.: 13/537,385

(22) Filed: Jun. 29, 2012

(65) Prior Publication Data

US 2014/0006365 A1 Jan. 2, 2014

(51) Int. Cl.
*G06F 17/30* (2006.01)
*G06F 19/18* (2011.01)
*G06F 19/24* (2011.01)

(52) U.S. Cl.
CPC .......... *G06F 17/30864* (2013.01); *G06F 19/18* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 6,401,043 B1 | 6/2002 | Stanton, Jr. | |
| 6,468,744 B1 | 10/2002 | Cronin | |
| 6,609,085 B1 * | 8/2003 | Uemura et al. | ............... 702/189 |
| 7,017,186 B2 | 3/2006 | Day | |
| 8,012,740 B2 | 9/2011 | Hillis | |
| 8,055,603 B2 | 11/2011 | Angell | |
| 8,078,407 B1 | 12/2011 | Brown | |
| 8,126,655 B2 | 2/2012 | Katoh et al. | |
| 8,145,582 B2 | 3/2012 | Angell | |
| 8,296,268 B2 * | 10/2012 | Ingles et al. | .................. 707/672 |
| 8,340,914 B2 | 12/2012 | Gatewood | |
| 2003/0194711 A1 | 10/2003 | Zapala | |
| 2003/0195706 A1 | 10/2003 | Korenberg | |
| 2003/0220844 A1 | 11/2003 | Marnellos | |
| 2003/0233197 A1 | 12/2003 | Padilla et al. | |
| 2004/0153255 A1 | 8/2004 | Ahn | |
| 2004/0224334 A1 | 11/2004 | Shibuya | |
| 2005/0019787 A1 | 1/2005 | Berno | |
| 2005/0267693 A1 | 12/2005 | Allard et al. | |
| 2006/0020398 A1 | 1/2006 | Vernon et al. | |

(Continued)

FOREIGN PATENT DOCUMENTS

| | | |
|---|---|---|
| CN | 101430742 A | 5/2009 |
| CN | 102081707 A | 6/2011 |

(Continued)

OTHER PUBLICATIONS

Ernst, J. and Bar-Joseph, Z. Stem: a tool for the analysis of short time series gene expression data. BMC Bioinformatics, 7:191, 2006.*

(Continued)

*Primary Examiner* — Robert Beausoliel, Jr.
*Assistant Examiner* — Richard Bowen
(74) *Attorney, Agent, or Firm* — Brown & Michaels, PC; John R. Pivnichny (57) ABSTRACT

A method, computer program product and system of minimizing epigenetic surprisal data either by comparing epigenetic surprisal data to a fixed baseline epigenetic data, so that all of the comparisons were made to the same baseline epigenetic data or by comparing epigenetic surprisal data to a rolling baseline of epigenetic surprisal data—that is, after each comparison the baseline is changed to the data from the time point which had been compared previously.

45 Claims, 8 Drawing Sheets

(56) References Cited

U.S. PATENT DOCUMENTS

| | | | |
|---|---|---|---|
| 2006/0166224 A1 | 7/2006 | Norviel | |
| 2007/0276610 A1 | 11/2007 | Korenberg | |
| 2007/0282538 A1 | 12/2007 | Narasimhan et al. | |
| 2008/0077607 A1* | 3/2008 | Gatawood et al. | 707/101 |
| 2008/0154512 A1* | 6/2008 | Leong | 702/19 |
| 2008/0294692 A1 | 11/2008 | Angell et al. | |
| 2009/0006002 A1* | 1/2009 | Honisch et al. | 702/20 |
| 2009/0018994 A1* | 1/2009 | Hajdukiewicz | 707/2 |
| 2009/0158211 A1 | 6/2009 | Gogolak | |
| 2009/0182862 A1* | 7/2009 | Thomson et al. | 709/224 |
| 2010/0241670 A1* | 9/2010 | Justice et al. | 707/803 |
| 2011/0029341 A1* | 2/2011 | Muse et al. | 705/7 |
| 2011/0087436 A1* | 4/2011 | Klapa et al. | 702/19 |
| 2011/0213212 A1* | 9/2011 | Al-Ali | 600/300 |
| 2011/0319298 A1 | 12/2011 | Benner et al. | |
| 2012/0066001 A1 | 3/2012 | Sanborn | |
| 2012/0185612 A1* | 7/2012 | Zhang et al. | 709/247 |
| 2012/0197533 A1 | 8/2012 | Nazarenko | |
| 2012/0230326 A1 | 9/2012 | Ganeshalingam et al. | |
| 2013/0024435 A1* | 1/2013 | Poirier et al. | 707/695 |
| 2013/0262465 A1 | 10/2013 | Galle et al. | |

FOREIGN PATENT DOCUMENTS

| | | |
|---|---|---|
| CN | 102222174 A | 10/2011 |
| JP | 2004240975 | 8/2004 |
| WO | 02063479 A1 | 8/2002 |
| WO | 03081509 A2 | 10/2003 |
| WO | 03083442 A2 | 10/2003 |
| WO | 2005107412 A2 | 11/2005 |
| WO | 2010072382 A1 | 7/2010 |
| WO | 2011076130 A1 | 6/2011 |

OTHER PUBLICATIONS

Ernst, J., Nau, G.J. and Bar-Joseph, Z. Clustering Short Time Series Gene Expression Data. Bioinformatics, 21 Suppl. 1, pp. i159-i168, 2005.*

Abe, Hidenao et al. "Implementing an Integrated Time-Series Data Mining Environment Based on Temporal Pattern Extraction Methods: A Case Study of an Interferon Therapy Risk Mining for Chronic Hepatitis," 2006, Springer Berlin Heidelberg, New Frontiers in Artificial Intelligence, Lecture Notes in Computer Science, vol. 4012, pp. 425-435.*

PCT Search Report for PCT/IB2013/052012 mailed Aug. 15, 2013; 10 pages.

Craig, A.G. et al; "Ordering of cosmid clones covering the *Herpes simplex virus* type 1 (HSV-1) genome: a test case for fingerprinting by hybridisation"; Nucleic Acids Research, vol. 18, No. 9; 1990; pp. 2653-2660.

ssahaSNP: Sequence Search and Alignment by Hashing Algorithm; http://www.sanger.ac.uk/resources/software/ssahashp/; Wellcome Trust Sanger Institute; 2011; 2 pages.

He, Q. et al; A Variable Selection Method for Genome-wide Association Studies; Dept. of Biostatistics, Univ. of North Carolina; Oct. 2010; pp. 1-8.

GWASelect: A Variable Selection Method for Genomewide Association Studies ; http://www.bios.unc.edu/~lin/software/GWASelect; at least as early as Feb. 23, 2010; 1 page.

Ruschendorf, F. et al.; "ALOHOMORA: a tool for linkage analysis using 10K SNP Array Data"; BioInformatics Applications Note; vol. 21, No. 9, 2005; pp. 2123-2125.

Hoffmann K. et al.; "easyLINKAGE-Plus—automated linkage analyses using large-scale SNP data"; BioInformatics Applications Note, vol. 21 No. 17 2005. pages 3565-3567.

International HapMap Project; http://hapmap.ncbi.nlm.nih.gov/cgi-perl/gbrowse/hapmap27_B36/; Feb. 2009; 2 pages.

International HapMap Project: http://en.wikipedia.org/wiki/International_HapMap_Project; Oct. 27, 2002; 4 pages.

Jorde, L. B. et al.; Genetic variation, classification and 'race'; 2004; Nature Genetics 36 (11 Suppl): S28-S33; 8 pages.

Tishkoff, S. A. et al., Implications of biogeography of human populations for 'race' and medicine; Nature Genetics 36 (11 Suppl): S21-7; 2004; 9 pages.

International HapMap Project; http://hapmap.ncbi.nlm.nih.gov/; 2009; 3 pages.

Human Genome Project Information; http://www.ornl.gov/sci/techresources/Human_Genome/fag/fags1.shtml; 1990; 9 pages.

Wacker, S.A. et al; Using transcriptome sequencing to identify mechanisms of drug action and resistance; Nature Chemical Biology; Feb. 2012; 37 pages.

Brandon, M.G. et al., "Data structures and compression algorithms for genomic sequence data"; BioInformatics—vol. 25: 2009; pp. 1731-1738.

Cao, M.D. et al.: "Agenome alignment algorithm based on compression"; BMC Cioinformatics; 2010; 16 pages.

Christley, S. et al., "Human genomes as email attachments"; Bio Informatics—vol. 25; 2009; pp. 274-275.

Human Genome Diversity Project; http://wikipedia.org/wiki/Human_Genome_Diversity_Project; 2012; 5 pages.

Cavalli-Sforza, L., "The Human Genome Diversity Project: past, present and future";Nature Reviews/Genetics; Apr. 2005; 8 pages.

Rosenberg, N. A.; "Standardized subsets of the HGDP-CEPH Human Genome Diversity Cell Line Panel, accounting for atypical and duplicated samples and pairs of close relatives"; Annals of Human Genetics; Feb. 2006; 40 pages.

Amigo, J. et al.; SPSmart: adapting population based SNP genotype databases for fast and comprehensive web access; BMC Bioinformatics; Oct. 2008; 6 pages.

Li, J.A. et al; "Worldwide Human Relationships Inferred from Genome-Wide Patterns of Variation"; Science—vol. 319; 2008; 6 pages.

Novembre, J. et al., "Genes mirror geography within Europe"; Nature; Nov. 2008; 13 pages.

Centroid definition , "The Penguin Dictionary of Mathematics" 2008.

Kohane, I et al.; "Health Information Identification and De-Identification Toolkit"; Proc AMIA Symp.; 1998; pp. 356-360.

Malin, B.; "An Evaluation of the Current State of Genomic Data Privacy Protection Technology and a Roadmap for the Future"; J Am Med Inform Assoc.; Dec. 2005; pp. 28-34.

Kapis, K. et al.; "Security Mechanisms for Electronic Patient Records in Mobile Intelligent Services"; MEDINF; Craiova Medicala Journal; Oct. 2003; 4 pages.

Heurix, J. et al.; "A Hybrid Approach Integrating Encryption and Pseudonymization for Protecting Electronic Health Records"; Proceedings of the Eighth IASTED International Conference on Biomedical Engineering; 2001; 8 pages.

Weerasinghe, D. et al.; "Securing electronic health records with novel mobile encryption schemes"; Int. J. Electronic Healthcare; 2007, vol. 3 No. 4; pp. 395-416.

Dean, J. et al; MapReduce: Simplified Data Processing on Large Clusters; OSDI; 2004; pp. 1-13.

Hedlund, B.; Understanding Hadoop Clusters and the Network; http://bradhedlund.com/?p=3108; Sep. 10, 2011; 26 pages.

Titmus, M. et al.; Answering the demands of digital genomics; Concurrency and Computation: Practice and Experience; Aug. 2012; 12 pages.

Schadt, E. et al.; Computational solutions to large-scale data management and analysis; Nat. Rev. Genet; Sep. 2010; 22 pages.

Shvachko, K. et al.; The Hadoop Distributed File System; IEEE; 2010: 10 pages.

International PCT Search Report for PCT/IB2013/055173; Jan. 2, 2014; 9 pages.

Hillman-Jackson, J. et al; "Using Galaxy to Perform Large-Scale Interactive Data Analyses"; Current Protocols in Bioinformatics, Jun. 2012; 47 pages.

Galaxy Wiki; http://wiki.g2.bx.psu.edu/; At least as early as 2011; 2 pages.

Galaxy Wiki; "Custom Genomes"; http://wiki.g2.bx.psu.edu/Learn/CustomGenomes; At least as early as Apr. 2012; 4 pages.

Galaxy—Rous; "Comparing genomic intervals using galaxy"; http://rous.mit.edu/index.php/Comparing_genomic_intervals_using_galaxy; At least as early as Jan. 27, 2010; 2 pages.

(56) References Cited

OTHER PUBLICATIONS

The Galaxy Team; "An Introduction to Galaxy"; http://UseGalaxy.org; Jul. 28, 2011; 107 pages.

Christopher Schmid; "Reviews in Computational Biology Comparing Epigenetic Maps: Computational tasks and aspects of data analysis"; Swiss Tropical and Public Health Institute; May 2, 2011; 31 pages.

Grumbach, S. et al.; A New Challenge for Compression Algorithms: Genetic Sequences; Genetic Sequences; 1994;12 pages.

International PCT Search Report for PCT/IB2013/052011; Jun. 18, 2013; 8 pages.

Haefliger et al. "Four Novel Members of the Connexin Family of Gap Junction Proteins." The Journal of Biological Chemistry. vol. 267.

Abe, Hidenao et al., "Implementing an Integrated Time-Series Data Mining Environment Based on Temporal Pattern Extraction Methods: A Case Study of Interferon Therapy Risk Mining for Chronic Hepatitis," 2006, Springer Berlin Heidelberg, New Frontiers in Artificial Intelligence, Lecture Notes in Computer Science, vol. 4012, pp. 425-435.

Haefliger et al. "Four Novel Members of the Connexin Family of Gap Junction Proteins." The Journal of Biological Chemistry. vol. 267, Jan. 25, 1992.

\* cited by examiner

Fig. 7
At Destination:

| Reference Epigenetic Map/Baseline Suprisal Data | | | |
|---|---|---|---|
| Epigenetic Mark | Cell Type | Alteration | Gene |
| DNA methylation | T-cells | CpG island hypomethylation | A1A1 |

Time Period: Time 0 - Time X      +

| Epigenetic Surprisal Data of Organism @ Time 0 | | | |
|---|---|---|---|
| Epigenetic Mark | Cell Type | Alteration | Gene |
| DNA methylation | B-cells | CpG island hypomethylation | B2B3 |
| Histone Modification | Monocytes | Gain of H4 acetylation | C5D2 |

| Epigenetic Surprisal Data of Organism @ Time X | | | |
|---|---|---|---|
| Epigenetic Mark | Cell Type | Alteration | Gene |
| DNA methylation | B-cells | CpG island hypomethylation | B2B3 |
| Histone Modification | Monocytes | Gain of H4 acetylation | C5D2 |
| Histone Modification | Monocytes | Gain of H4 acetylation | C5D6 |

| Epigenetic Map of Organism at Time X | | | |
|---|---|---|---|
| Epigenetic Mark | Cell Type | Alteration | Gene |
| DNA methylation | T-cells | CpG island hypomethylation | A1A1 |
| DNA methylation | B-cells | CpG island hypomethylation | B2B3 |
| Histone Modification | Monocytes | Gain of H4 acetylation | C5D2 |
| Histone Modification | Monocytes | Gain of H4 acetylation | C5D6 |

Fig. 8

MINIMIZATION OF EPIGENETIC SURPRISAL DATA OF EPIGENETIC DATA WITHIN A TIME SERIES

BACKGROUND

The present invention relates to minimizing epigenetic surprisal data, and more specifically to minimizing epigenetic surprisal data within a time series or time period.

Epigenetics includes the study of heritable changes in gene expression that are not due to changes in DNA sequence, in other words, all modifications to genes other than changes to the DNA sequence itself Examples of modifications are DNA methylation, histone modification, chromatic accessibility, acetylation, phosphorylation, ubiquitination, ADP-ribosylation and others. The modifications alter the chromatin structure of the DNA and its accessibility, and therefore the regulation of gene expression patterns. The pattern of gene expression can also be modified by exogenous influences, such as environmental influences including nutrition. These modifications can persist throughout an organism's lifetime and be passed onto to future generations.

Epigenetic maps include a map or display of what modifications have been made to specific chromosomes and/or the entire genome of an organism. Epigenetic maps are produced by massively parallel sequencing of a portion of an organism's genome or the entire genome and mapping the sequence to a reference genome assembly to infer genomic coordinates of modifications. Within the study of epigenetics it is beneficial to compare an epigenetic map taken at a point in time and compare it to an epigenetic map generated at another point of time to determine what changes have taken place in a specific time period. For an entire genome of an organism, the amount of data associated with these changes can be infinitely large. Furthermore, the transfer of such information can take up significant space and time over a network data processing system.

SUMMARY

According to one embodiment of the present invention a method of minimizing epigenetic surprisal data. The method comprising: a computer receiving a request for an epigenetic time series analysis comprising at least an indication of a baseline epigenetic surprisal data and a period of time for the epigenetic time series analysis; the computer retrieving a baseline epigenetic surprisal data and epigenetic surprisal data for at least one time point within the time period from a repository; and the computer comparing the at least one epigenetic surprisal data within the time period to the baseline epigenetic surprisal data, producing at least one epigenetic modification difference, the computer storing the at least one epigenetic modification difference in a repository; and repeating the method for all epigenetic surprisal data time points within the time period.

According to another embodiment of the present invention, a method of minimizing epigenetic surprisal data. The method comprising: a computer receiving a request for an epigenetic time series analysis comprising at least a period of time for the epigenetic time series analysis; the computer retrieving epigenetic data at time points within the time period from a repository; the computer designating a first epigenetic data at a time point within the time period as a baseline; the computer comparing the baseline to a next epigenetic data and storing the difference in a repository as epigenetic surprisal data; the computer designating the next epigenetic data from the comparison as the baseline, and the computer repeating the step of comparing and designating, until all epigenetic data in the time period have been compared.

According to another embodiment of the present invention, a computer program product for minimizing epigenetic surprisal data. The computer program product comprising: one or more computer-readable, tangible storage devices; program instructions, stored on at least one of the one or more storage devices, to receive a request for an epigenetic time series analysis comprising at least an indication of a baseline epigenetic surprisal data and a period of time for the epigenetic time series analysis; program instructions, stored on at least one of the one or more storage devices, to retrieve a baseline epigenetic surprisal data and epigenetic surprisal data for at least one time point within the time period from a repository; and program instructions, stored on at least one of the one or more storage devices, to compare the at least one epigenetic surprisal data within the time period to the baseline epigenetic surprisal data, producing at least one epigenetic modification difference; program instructions, stored on at least one of the one or more storage devices, to store the at least one epigenetic modification difference in a repository; and program instructions, stored on at least one of the one or more storage devices, to repeat the method for all epigenetic surprisal data time points within the time period.

According to another embodiment of the present invention, a computer program product for minimizing epigenetic surprisal data. The computer program product comprising: one or more computer-readable, tangible storage devices; program instructions, stored on at least one of the one or more storage devices, to a receive a request for an epigenetic time series analysis comprising at least a period of time for the epigenetic time series analysis; program instructions, stored on at least one of the one or more storage devices, to retrieve epigenetic data at time points within the time period from a repository; program instructions, stored on at least one of the one or more storage devices, to designate a first epigenetic data at a time point within the time period as a baseline; program instructions, stored on at least one of the one or more storage devices, to compare the baseline to a next epigenetic data and storing the difference in a repository as epigenetic surprisal data; program instructions, stored on at least one of the one or more storage devices, to designate the next epigenetic data from the comparison as the baseline, and the program instructions, stored on at least one of the one or more storage devices, to repeat the step of comparing and designating, until all epigenetic data in the time period have been compared.

According to an embodiment of the present invention, a computer system for minimizing surprisal data. The computer system comprising: one or more processors, one or more computer-readable memories and one or more computer-readable, tangible storage devices; program instructions, stored on at least one of the one or more storage devices for execution by at least one of the one or more processors via at least one of the one or more memories, to receive a request for an epigenetic time series analysis comprising at least an indication of a baseline epigenetic surprisal data and a period of time for the epigenetic time series analysis; program instructions, stored on at least one of the one or more storage devices for execution by at least one of the one or more processors via at least one of the one or more memories, to retrieve a baseline epigenetic surprisal data and epigenetic surprisal data for at least one time point within the time period from a repository; and program instructions, stored on at least one of the one or more storage devices for execution by at least one of the one or more processors via at least one of the one or more memories, to compare the at least one epigenetic surprisal data within the time period to the baseline epigenetic surprisal data, producing at least one epigenetic modification difference; program instructions, stored on at least one of the one or more storage devices for execution by at least one of the one or more processors via at least one of the one or more memories, to store the at least one epigenetic modification difference in a repository; and program instructions, stored on at least one of the one or more storage devices for execution by at least one of the one or more processors via at least one of the one or more memories, to repeat the method for all epigenetic surprisal data time points within the time period.

According to another embodiment of the present invention, a computer system for minimizing epigenetic surprisal data. The computer system comprising: one or more processors, one or more computer-readable memories and one or more computer-readable, tangible storage devices; program instructions, stored on at least one of the one or more storage devices for execution by at least one of the one or more processors via at least one of the one or more memories, to a receive a request for an epigenetic time series analysis comprising at least a period of time for the epigenetic time series analysis; program instructions, stored on at least one of the one or more storage devices for execution by at least one of the one or more processors via at least one of the one or more memories, to retrieve epigenetic data at time points within the time period from a repository; program instructions, stored on at least one of the one or more storage devices for execution by at least one of the one or more processors via at least one of the one or more memories, to designate a first epigenetic data at a time point within the time period as a baseline; program instructions, stored on at least one of the one or more storage devices for execution by at least one of the one or more processors via at least one of the one or more memories, to compare the baseline to a next epigenetic data and storing the difference in a repository as epigenetic surprisal data; program instructions, stored on at least one of the one or more storage devices for execution by at least one of the one or more processors via at least one of the one or more memories, to designate the next epigenetic data from the comparison as the baseline, and program instructions, stored on at least one of the one or more storage devices for execution by at least one of the one or more processors via at least one of the one or more memories, to repeat the step of comparing and designating, until all epigenetic data in the time period have been compared.

DETAILED DESCRIPTION

The illustrative embodiments of the present invention recognize that epigenetic modifications to an organism's genome vary through time and that by attempting to look at all epigenetic modifications through a time period can result in a significant amount of data that has to managed and sent over a network processing system. The illustrative embodiments also recognize that by comparing epigenetic modifications to other epigenetic modifications within a time period at multiple points within the time period will reduce the "surprisal data" of epigenetic modifications. The illustrative embodiments also recognize that by comparing epigenetic modifications to a reference epigenetic map or a baseline epigenetic map, the data will be reduced down to the "surprisal data" which are "unlikely" or "surprising" relative to a baseline epigenetic map or a reference epigenetic map of modifications. Epigenetic modifications may include, but are not limited to DNA methylation, histone modification, chromatic accessibility, acetylation, phosphorylation, ubiquitination, and ADP-ribosylation. The epigenetic modifications alter the chromatin structure of the DNA and its accessibility, and therefore the regulation of gene expression patterns. The illustrative embodiments also recognize that by pairing epigenetic surprisal data within a time period, comparing the epigenetic surprisal data within the pair and then comparing the epigenetic surprisal pair data incrementally to other epigenetic surprisal pairs within the time period will yield a very small amount of epigenetic surprisal data, minimizing the epigenetic surprisal data for analysis and transmission over a network processing system.

Figure 1:
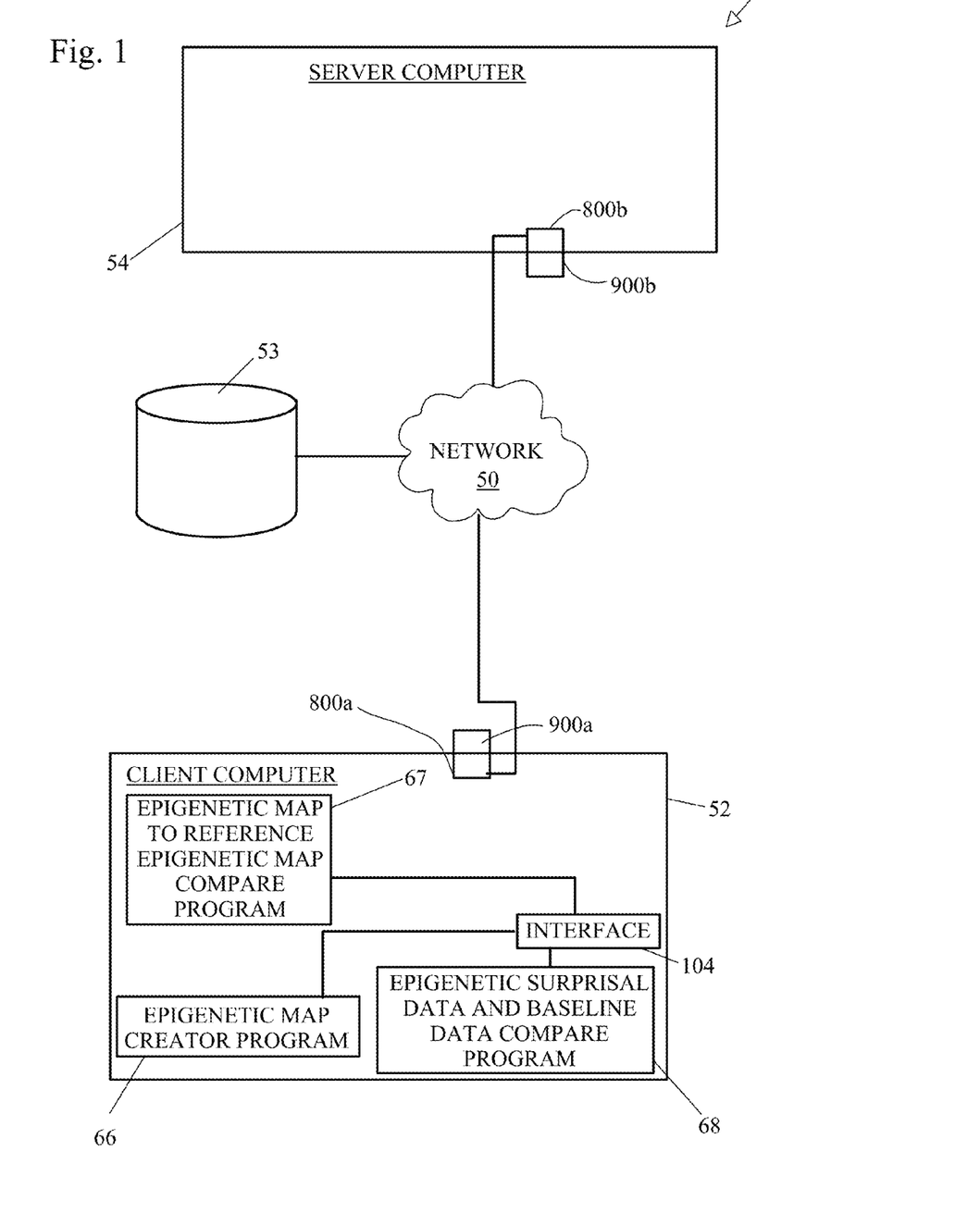
FIG. 1 depicts an exemplary diagram of a possible data processing environment in which illustrative embodiments may be implemented.

FIG. 1 is an exemplary diagram of a possible data processing environment provided in which illustrative embodiments may be implemented. It should be appreciated that FIG. 1 is only exemplary and is not intended to assert or imply any limitation with regard to the environments in which different embodiments may be implemented. Many modifications to the depicted environments may be made.

Referring to FIG. 1, network data processing system 51 is a network of computers in which illustrative embodiments may be implemented. Network data processing system 51 contains network 50, which is the medium used to provide communication links between various devices and computers connected together within network data processing system 51. Network 50 may include connections, such as wire, wireless communication links, or fiber optic cables.

In the depicted example, a client computer 52, server computer 54, and a repository 53 connect to network 50. In other exemplary embodiments, network data processing system 51 may include additional client computers, storage devices, server computers, and other devices not shown. The client computer 52 includes a set of internal components 800a and a set of external components 900a, further illustrated in FIG. 8. The client computer 52 may be, for example, a mobile device, a cell phone, a personal digital assistant, a netbook, a laptop computer, a tablet computer, a desktop computer, a sequencing machine or any other type of computing device.

Client computer 52 may contain an interface 104. The interface can be, for example, a command line interface, a graphical user interface (GUI), or a web user interface (WUI).

The interface may be used, for example for viewing a reference epigenetic map, a baseline epigenetic map, epigenetic surprisal data, an epigenetic map at time point from a repository. The interface may also accept an input regarding time period, reference epigenetic map and/or baseline epigenetic map.

In the depicted example, server computer 54 provides information, such as boot files, operating system images, and applications to client computer 52. Server computer 54 can compute the information locally or extract the information from other computers on network 50. Server computer 54 includes a set of internal components 800b and a set of external components 900b illustrated in FIG. 8.

Figure 8:
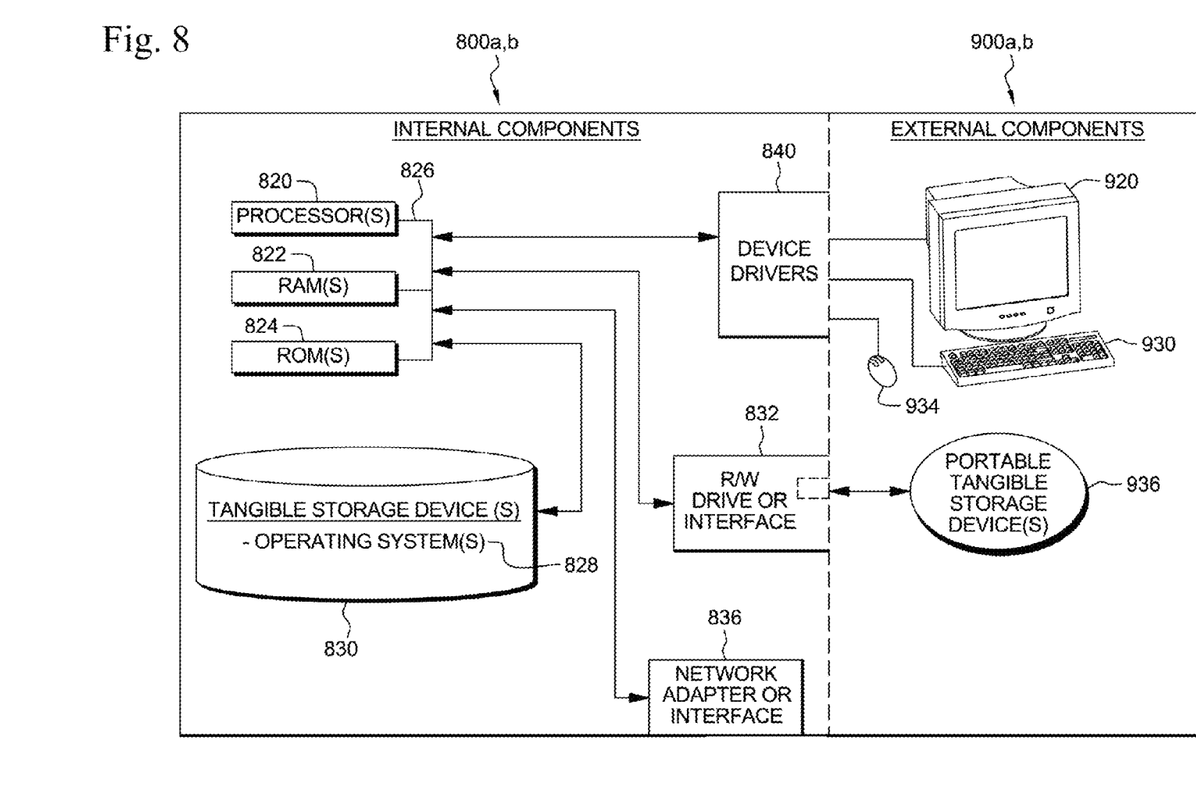
FIG. 8 illustrates internal and external components of a client computer and a server computer in which illustrative embodiments may be implemented.

Program code, reference epigenetic maps, baseline epigenetic maps, and programs such as an epigenetic map to reference epigenetic map compare program 67, an epigenetic map creator program 66, and/or an epigenetic surprisal data and baseline data compare program 68 may be stored on at least one of one or more computer-readable tangible storage devices 830 shown in FIG. 8, on at least one of one or more portable computer-readable tangible storage devices 936 as shown in FIG. 8, or repository 53 connected to network 50, or downloaded to a data processing system or other device for use. For example, program code, reference epigenetic maps, baseline epigenetic maps, epigenetic map to reference epigenetic map compare program 67, epigenetic map creator program 66, and/or epigenetic surprisal data and baseline data compare program 68 may be stored on at least one of one or more tangible storage devices 830 on server computer 54 and downloaded to client computer 52 over network 50 for use on client computer 52. Alternatively, server computer 54 can be a web server, and the program code, reference epigenetic maps, baseline epigenetic maps, and programs such as an epigenetic map to reference epigenetic map compare program 67, an epigenetic map creator program 66, and/or an epigenetic surprisal data and baseline data compare program 68 may be stored on at least one of the one or more tangible storage devices 830 on server computer 54 and accessed on client computer 52. Epigenetic map to reference epigenetic map compare program 67, epigenetic map creator program 66, and/or epigenetic surprisal data and baseline data compare program 68 can be accessed on client computer 52 through interface 104. In other exemplary embodiments, the program code, reference epigenetic maps, baseline epigenetic maps, and programs such as an epigenetic map to reference epigenetic map compare program 67, an epigenetic map creator program 66, and/or an epigenetic surprisal data and baseline data compare program 68 may be stored on at least one of one or more computer-readable tangible storage devices 830 on client computer 52 or distributed between two or more servers.

Figure 2:
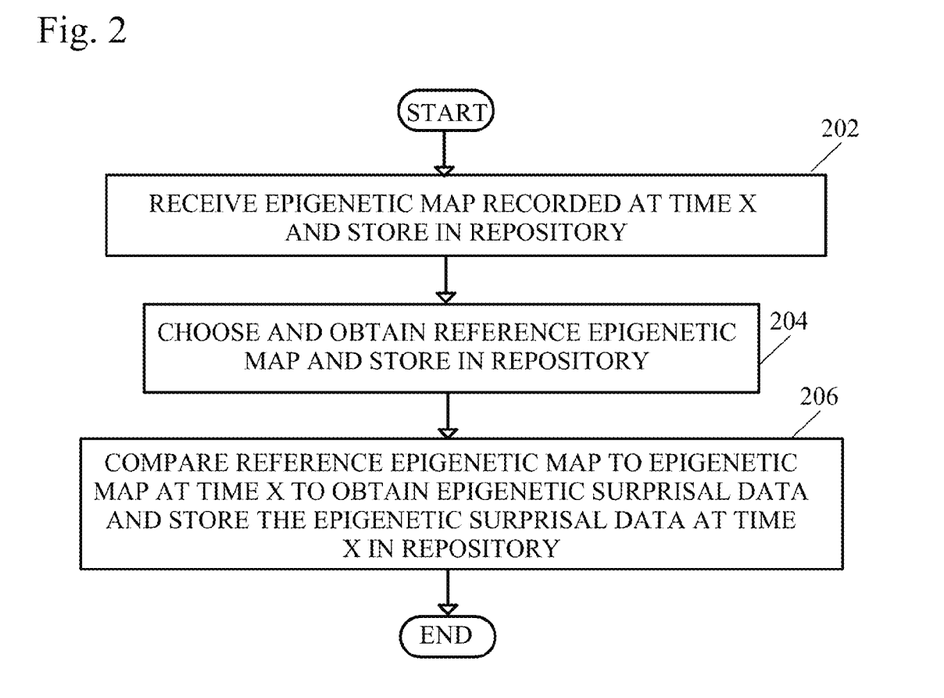
FIG. 2 shows a flowchart of a method of building a repository of epigenetic surprisal data at different time points.

FIG. 2 shows a flowchart of a method of building a repository of epigenetic surprisal data at different time points.

In a first step, an epigenetic map of an organism recorded at a given time (represented by time x) is received, and stored in a repository at a source (step 202), for example in repository 53, by the epigenetic map to reference epigenetic map compare program 67 as shown in FIG. 1. The designation "x" may be any number or other designation desired, for example an arbitrary integer, or a date or time indicator, etc. The organism may be a fungus, microorganism, human, animal or plant.

Based on the organism from which the epigenetic map is derived, an epigenetic map to reference epigenetic map compare program 67 chooses and obtains at least one reference epigenetic map, and stores the reference epigenetic map in a repository (step 204). Alternatively, the epigenetic map to reference epigenetic map compare program 67 may receive an input from a user regarding what specific reference epigenetic map is to be chosen and obtained.

A reference epigenetic map is an epigenetic map database which includes numerous epigenetic maps combined into one map. The details of the epigenetic maps may not represent any one specific individual's epigenetic map of their genome. They serve as a starting point for broad comparisons across a specific species, since the basic set of genes and genomic regulator regions that control the development and maintenance of the biological structure and processes are all essentially the same within a species, and the epigenetic modifications that take place may be similar. In other words, the reference epigenetic map can be a representative example of a species' epigenetic modifications of their genome.

Alternatively, the reference epigenetic map may be derived from the same individual, or a related individual, to the organism from which the epigenetic map was derived at time x (step 202). The reference epigenetic map may have been stored in a repository and derived from the individual at a time prior to time x.

The reference epigenetic map may be tailored depending on the analysis that may take place after obtaining the epigenetic surprisal data. For example, the an epigenetic map to reference epigenetic map compare program 67 can limit the comparison to specific genes of the reference epigenetic map, ignoring other gene modifications that may occur in specific populations of a species.

The epigenetic map to reference epigenetic map compare program 67 compares the at least one epigenetic map at time x to the reference epigenetic map to obtain epigenetic surprisal data and stores only the epigenetic surprisal data in a repository 53 (step 206). The epigenetic surprisal data is defined as at least one epigenetic modification difference that provides an "unexpected value" relative to the normally expected value of the reference epigenetic map or epigenetic baseline surprisal data. In other words, the epigenetic surprisal data contains at least one epigenetic modification difference present when comparing the epigenetic map to the reference epigenetic map or to epigenetic baseline surprisal data. The epigenetic surprisal data that is actually stored in the repository preferably includes a location of the epigenetic modification difference within the reference epigenetic map.

Steps 202-206 repeat as epigenetic maps of organisms and specific individuals of organisms are received at different times. The epigenetic surprisal data at different times are stored in the repository.

Figure 3:
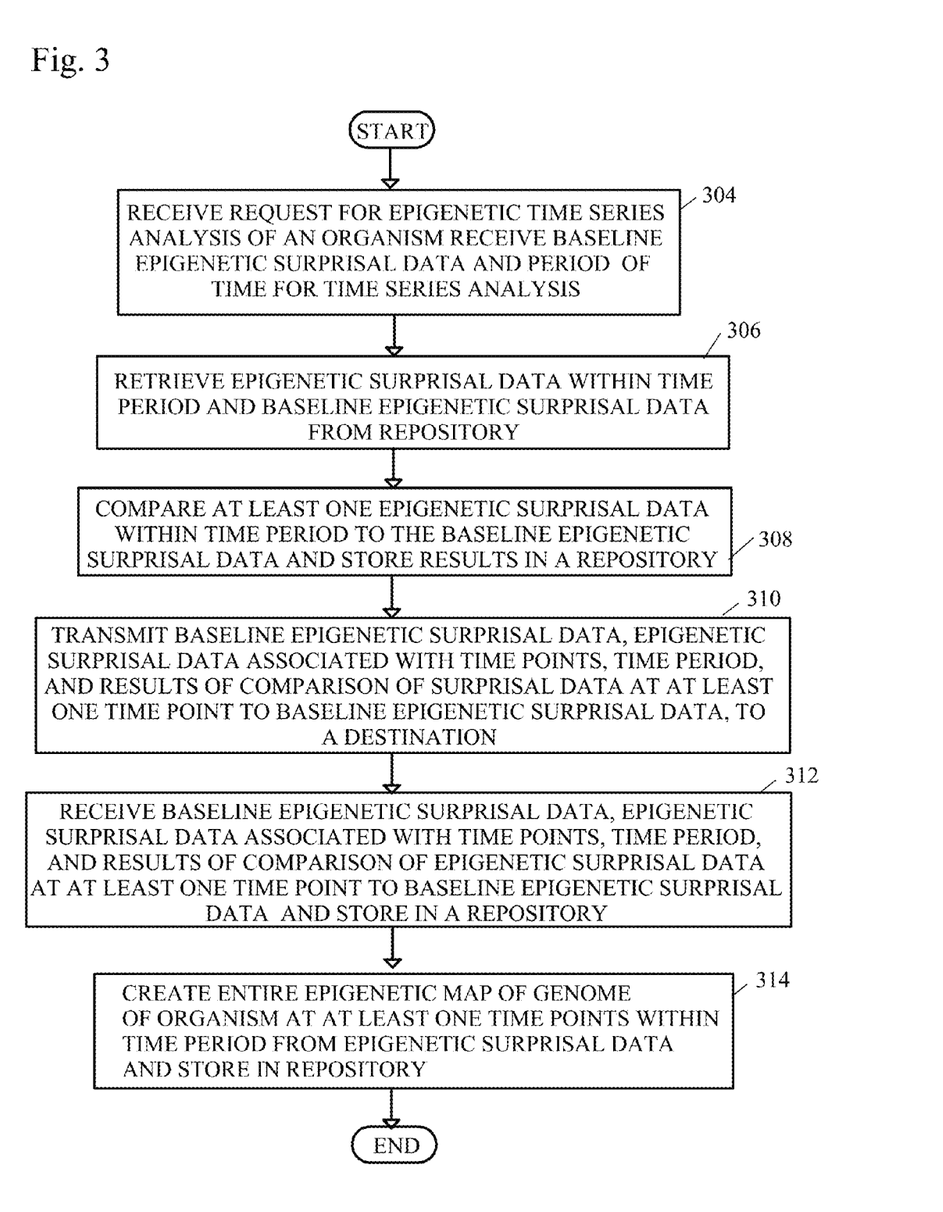
FIG. 3 shows a flowchart of a method of minimizing epigenetic surprisal data by comparing epigenetic surprisal data within a time period to a baseline of epigenetic surprisal data.

FIG. 3 shows a flowchart of a method of minimizing epigenetic surprisal data by comparing instances of epigenetic surprisal data derived at differing time points within a time period to a baseline of epigenetic surprisal data.

In a first step, an epigenetic surprisal data and baseline data compare program 68 receives a request from a user for an epigenetic time series analysis of an organism (step 304). An epigenetic time series analysis analyses the epigenetic changes that take place over a period of time.

The request comprises at least a time period and an indication of which epigenetic surprisal data should be used as the baseline for the time series analysis of the organism, for example through interface 104 shown in FIG. 1.

The epigenetic surprisal data and baseline data compare program 68 retrieves the baseline epigenetic surprisal data and the epigenetic surprisal data for the time points within the time period for an organism from a repository (step 306), for example repository 53 as shown in FIG. 1, for example the data from steps 202-206 as shown in FIG. 2.

The epigenetic surprisal data and baseline data compare program 68 compares at least one epigenetic surprisal data at a time point within the time period to the baseline epigenetic surprisal data, and stores the differences or results in a repository (step 308), for example repository 53 or another repository. In this step, the baseline epigenetic surprisal data acts effectively as a reference epigenetic map. The baseline epigenetic surprisal data provides a base or reference in which all other epigenetic surprisal data at different time points within the time period are measured. The epigenetic surprisal data is defined as at least one epigenetic modification difference that provides an "unexpected value" relative to the normally expected value of the reference epigenetic map or baseline epigenetic surprisal data. The epigenetic surprisal data that is actually stored in the repository preferably includes a location of the epigenetic modification difference within the baseline epigenetic surprisal data.

Figure 6:
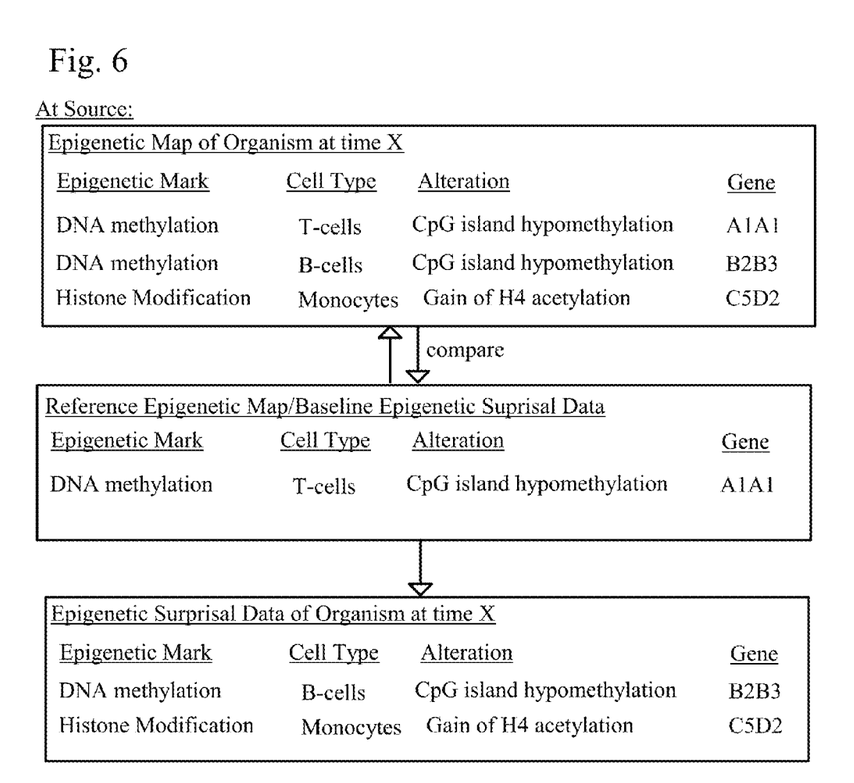
FIG. 6 shows a schematic of the comparison of an organism's epigenetic map to a reference epigenetic map to obtain epigenetic surprisal data.

FIG. 6 shows a schematic of the comparison of an organism's epigenetic map at a time "x" to a reference epigenetic map or baseline epigenetic map to obtain epigenetic surprisal data. In this example, the epigenetic map of the organism includes data of the type of epigenetic modification, the alteration/modification, the cell type, and the location of where the epigenetic modification took place. The epigenetic map of the organism includes DNA methylation at gene A1A1 and B2B3 and histone modification at gene C5D2. The reference epigenetic map or baseline epigenetic surprisal data includes DNA methylation at gene A1A1, therefore, the epigenetic surprisal data from the comparison at the source is the DNA methylation at gene B2B3 and histone modification at genet C5D2. It should be noted that instead of comparing the epigenetic map of the organism as shown in FIG. 6, the method may also compare epigenetic surprisal data of the organism to the baseline epigenetic surprisal data.

The amount of data and type of data shown in FIG. 6 is not limited to the data shown. The data shown in FIG. 6 is purely for example purposes and does not represent real data.

The baseline epigenetic surprisal data, epigenetic surprisal data associated with time points within the time period, the time period, and the differences or the results of the comparison of the epigenetic surprisal data at at least one point to the baseline epigenetic surprisal data, are transmitted to a destination (step 310) for example by an epigenetic surprisal data and baseline data compare program 68.

An epigenetic map creator program 66 receives the data transmitted in step 310—baseline epigenetic surprisal data, epigenetic surprisal data associated with time points within the time period, the time period, and the differences or the results of the comparison of the epigenetic surprisal data at at least one point to the baseline epigenetic surprisal data—and stores the data received in a repository, for example repository 53 or another repository at the destination (step 312).

The epigenetic map creator program 66 then creates an entire epigenetic map of a genome of the organism at at least one of the time points within the time period from the epigenetic surprisal data and stores the at least one epigenetic map in a repository (step 314).

Figure 7:
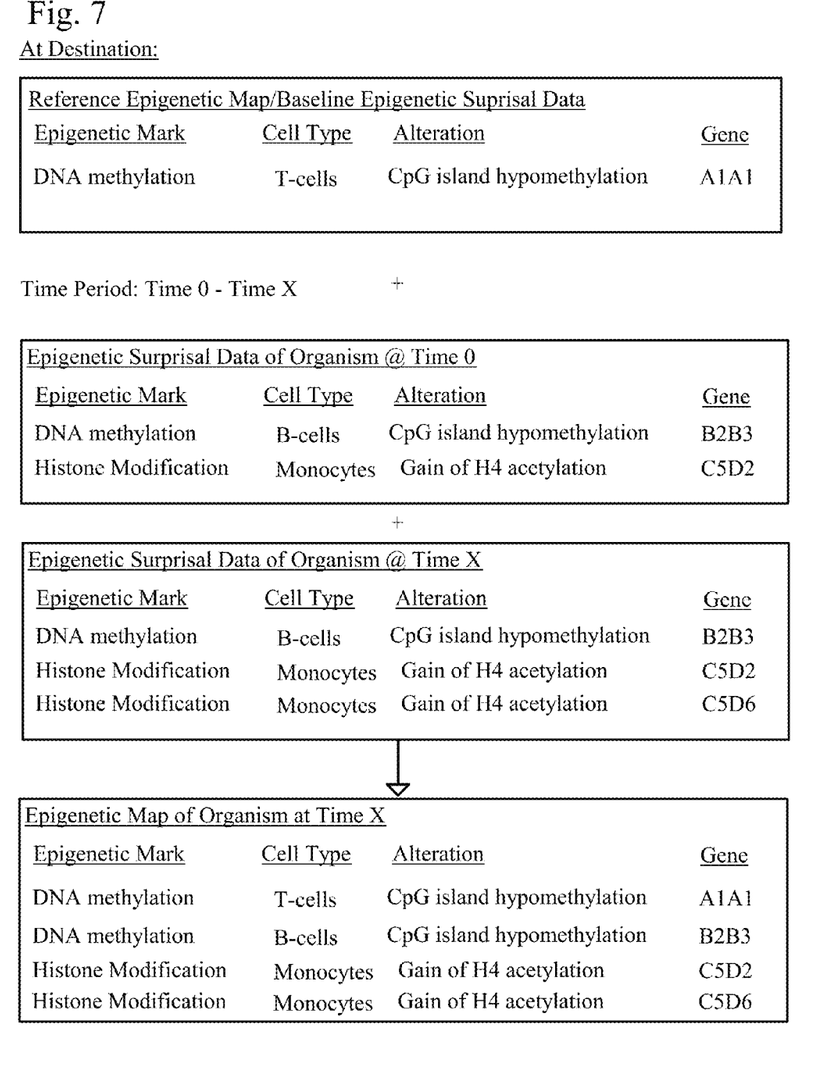
FIG. 7 shows a schematic of the re-creation of an organism's epigenetic genome at at least one time using an epigenetic reference genome and surprisal data.

FIG. 7 shows a schematic of the re-creation of an organism's epigenetic genome at at least one time (for example, time "X") using an epigenetic reference genome and epigenetic surprisal data. In this example, at the destination, a reference epigenetic map and/or baseline epigenetic surprisal data, an indication of the desired time period being from time 0 to time X, epigenetic surprisal data at time 0, and epigenetic surprisal data at time X has been received. The reference epigenetic map, baseline epigenetic surprisal data, and epigenetic surprisal data of the organism includes data of the type of epigenetic modification, the alteration/modification, the cell type, and the location of where the epigenetic modification took place.

If a user requests a complete epigenetic map at time X, for example, the reference epigenetic map which includes DNA methylation at gene A1A1 would be compared and combined with the epigenetic surprisal data of the organism at time X, which includes DNA methylation at gene B2B3 and histone modification at gene C5D2 and C5D6. The reference epigenetic map or baseline epigenetic surprisal data includes DNA methylation at gene A1A1, therefore, the complete epigenetic map at time X would include DNA methylation at gene A1A1 and gene B2B3 and histone modification at gene C5D2 and C5D6.

The amount of data and type of data shown in FIG. 7 is not limited to the data shown. The data shown in FIG. 7 is purely for example purposes and does not represent real data.

Figure 4:
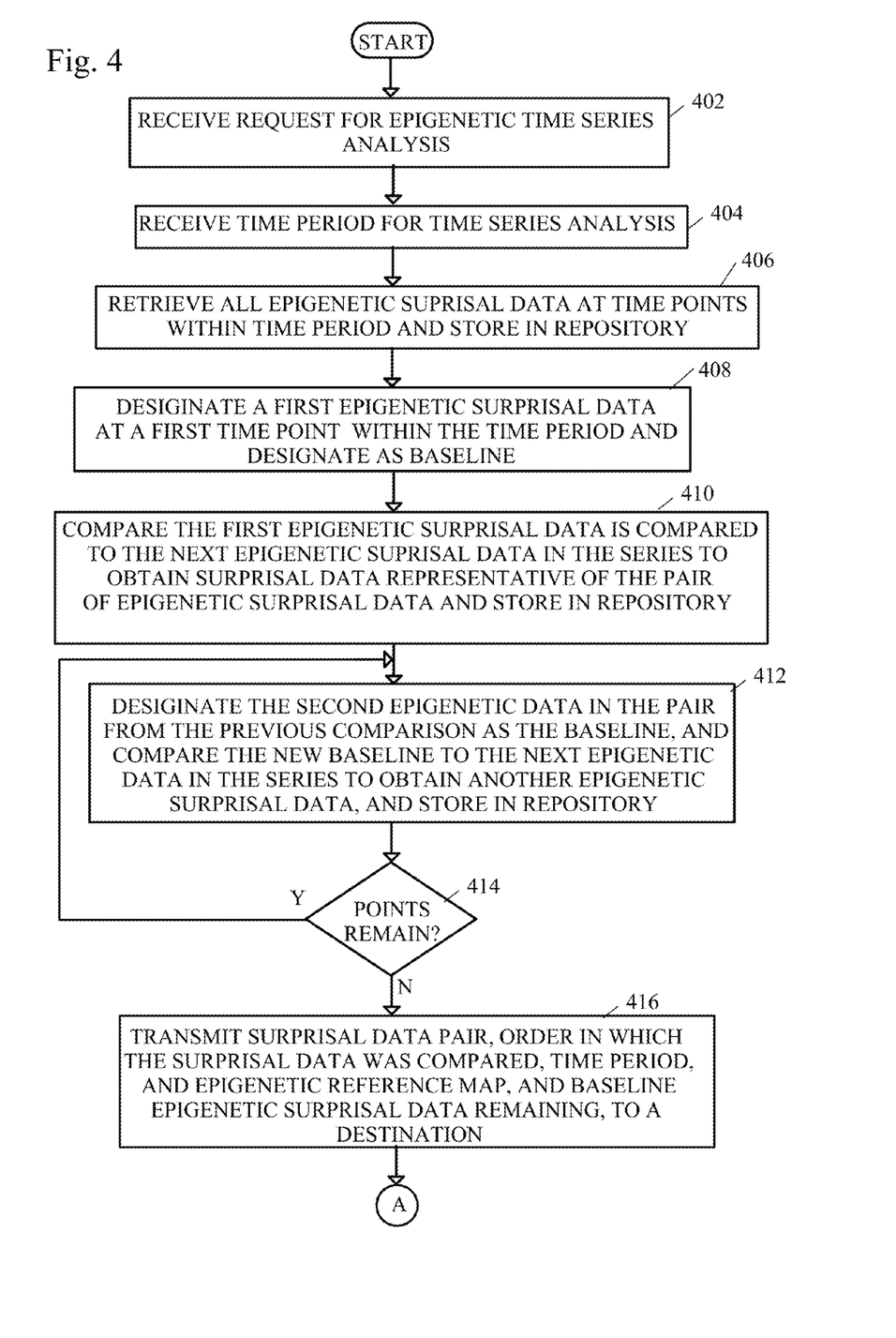
FIG. 4-5 shows a flowchart of a method of minimizing epigenetic surprisal data by comparing epigenetic surprisal data to other epigenetic surprisal data points with an incrementing baseline of surprisal data.
Figure 5:
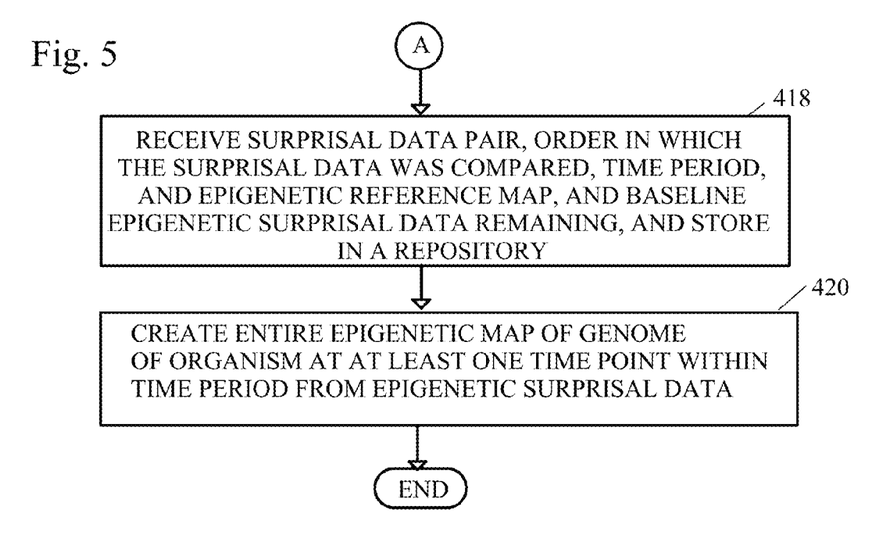

In the previous explanations, the baseline epigenetic data was fixed, so that all of the comparisons were made to the same baseline epigenetic data. FIGS. 4-5 shows a flowchart of another method of minimizing epigenetic surprisal data by comparing epigenetic surprisal data a rolling baseline of epigenetic surprisal data—that is, after each comparison the baseline is changed to the data from the time point which had been compared previously.

In a first step, an epigenetic surprisal data and baseline data compare program 68 receives a request from a user for an epigenetic time series analysis of an organism (step 402). An epigenetic time series analysis analyses the epigenetic changes that take place over a period of time.

The epigenetic surprisal data and baseline data compare program 68 receives a time period for the time series analysis of the organism from a user (step 404), for example through interface 104 shown in FIG. 1.

The epigenetic surprisal data and baseline data compare program 68 retrieves all epigenetic surprisal data at time points within time period and stores the data in a repository (step 406), for example repository 53 shown in FIG. 1.

The epigenetic surprisal data and baseline data compare program 68 starts with a first epigenetic surprisal data at a first time point within the time period, and uses that as a baseline for comparison with the epigenetic surprisal data at the next time point within the time period. (step 408).

It will be understood that the starting point could be the first epigenetic data, as described in this example, progressing forward through the time points in the time period or the method could start with the last time point and compare backward in time.

The first epigenetic surprisal data is compared to the next epigenetic surprisal data in the series to obtain differences or surprisal data representative of the pair of epigenetic surprisal data. The surprisal data representative of the pair of epigenetic surprisal data is stored in a repository (step 410).

Then, the method "rolls" the baseline forward—that is, the second epigenetic data in the pair from the previous comparison is designated as the baseline, and the method repeats by comparing the new baseline (i.e. second) to the next (i.e. third) epigenetic data in the series to obtain another epigenetic surprisal data, which is then stored in the repository (step 412).

If there are additional time points of epigenetic surprisal data remaining (step 414), repeat step 412, rolling the baseline forward and comparing again.

If there are no additional time points of epigenetic surprisal data remaining (step 414), the first designated pair, the baseline epigenetic surprisal data from each stepwise comparison, the order in which surprisal data was compared, the time period, and epigenetic reference map used to generate the surprisal data, are transmitted to a destination (step 416).

The first designated pair, the baseline epigenetic surprisal data from each stepwise comparison, the order in which surprisal data was compared, the time period, and epigenetic reference map used to generate the surprisal data, are received by an epigenetic map creator program 66, and stores the data in a repository, for example repository 53 or another repository at the destination (step 418).

The epigenetic map creator program 66 then recreates an entire epigenetic map of a genome of the organism at at least one of the time points within the time period from the epigenetic surprisal data and stores the at least one epigenetic map in a repository (step 420).

FIG. 8 illustrates internal and external components of client computer 52 and server computer 54 in which illustrative embodiments may be implemented. In FIG. 8, client computer 52 and server computer 54 include respective sets of internal components 800a, 800b, and external components 900a, 900b. Each of the sets of internal components 800a, 800b includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828, epigenetic map to reference epigenetic map compare program 67, epigenetic map creator program 66, and epigenetic surprisal data and baseline data compare program 68 are stored on one or more of the computer-readable tangible storage devices 830 for execution by one or more of the processors 820 via one or more of the RAMs 822 (which typically include cache memory). In the embodiment illustrated in FIG. 8, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800a, 800b also includes a R/W drive or interface 832 to read from and write to one or more portable computer-readable tangible storage devices 936 such as a CD-ROM, DVD, memory stick, magnetic tape, magnetic disk, optical disk or semiconductor storage device. Epigenetic map to reference epigenetic map compare program 67, epigenetic map creator program 66, and epigenetic surprisal data and baseline data compare program 68 can be stored on one or more of the portable computer-readable tangible storage devices 936, read via R/W drive or interface 832 and loaded into hard drive 830.

Each set of internal components 800a, 800b also includes a network adapter or interface 836 such as a TCP/IP adapter card. Epigenetic map to reference epigenetic map compare program 67, epigenetic map creator program 66, and epigenetic surprisal data and baseline data compare program 68 can be downloaded to client computer 52 and server computer 54 from an external computer via a network (for example, the Internet, a local area network or other, wide area network) and network adapter or interface 836. From the network adapter or interface 836, an epigenetic map to reference epigenetic map compare program 67, an epigenetic map creator program 66, and an epigenetic surprisal data and baseline data compare program 68 are loaded into hard drive 830. The network may comprise copper wires, optical fibers, wireless transmission, routers, firewalls, switches, gateway computers and/or edge servers.

Each of the sets of external components 900a, 900b includes a computer display monitor 920, a keyboard 930, and a computer mouse 934. Each of the sets of internal components 800a, 800b also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Epigenetic map to reference epigenetic map compare program 67, epigenetic map creator program 66, and epigenetic surprisal data and baseline data compare program 68 can be written in various programming languages including low-level, high-level, object-oriented or non object-oriented languages. Alternatively, the functions of an epigenetic map to reference epigenetic map compare program 67, an epigenetic map creator program 66, and an epigenetic surprisal data and baseline data compare program 68 can be implemented in whole or in part by computer circuits and other hardware (not shown).

Based on the foregoing, a computer system, method and program product have been disclosed for minimizing epigenetic surprisal data. However, numerous modifications and substitutions can be made without deviating from the scope of the present invention. Therefore, the present invention has been disclosed by way of example and not limitation.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method of minimizing epigenetic surprisal data comprising:
   a computer receiving a request for an epigenetic time series analysis comprising at least an indication of a baseline epigenetic surprisal data and a time period for the epigenetic time series analysis;
   the computer retrieving a baseline epigenetic surprisal data and epigenetic surprisal data for at least one time point within the time period from a repository; and
   the computer comparing the at least one epigenetic surprisal data comprising a location of an epigenetic modification, a time in which the epigenetic modification was collected and a type of epigenetic modification for the at least one time point within the time period to the baseline epigenetic surprisal data comprising a location of an epigenetic modification, a time in which the epigenetic modification was collected and a type of epigenetic modification, producing at least one epigenetic modification difference;
   the computer storing the at least one epigenetic modification difference in a repository; and
   repeating the method for all epigenetic surprisal data time points within the time period.

2. The method of claim 1, further comprising a computer recreating an epigenetic map of an organism at a specific time point within the time period by:
   retrieving an epigenetic surprisal data within the time period from the repository;
   retrieving baseline epigenetic surprisal data from the repository; and
   altering the baseline epigenetic surprisal data based on the epigenetic surprisal data at a specific time point by altering the map to include epigenetic modifications specified by the epigenetic surprisal data associated with a location; resulting in an entire epigenetic map of an organism at a specific time point within the time period.

3. The method of claim 1, further comprising prior to the computer receiving a request for an epigenetic time series analysis, the computer:
   receiving an epigenetic map at time x of an organism comprising epigenetic modifications;
   comparing the epigenetic map at time x to a reference epigenetic map, to find differences where epigenetic modifications of the organism at time x which are different from the epigenetic modifications of the reference epigenetic map; and
   the computer using the differences to create and store epigenetic surprisal data in a repository.

4. The method of claim 1, wherein the organism is an animal.

5. The method of claim 1, wherein the organism is a microorganism.

6. The method of claim 1, wherein the organism is a plant.

7. The method of claim 1, wherein the organism is a fungus.

8. The method of claim 1, wherein the epigenetic modification is generated by storing only differences between an epigenetic map at time x and a reference epigenetic map.

9. A method of minimizing epigenetic surprisal data comprising:
- a computer receiving a request for an epigenetic time series analysis comprising at least a a time period for the epigenetic time series analysis;
- the computer retrieving epigenetic surprisal data at time points within the time period from a repository, the epigenetic surprisal data comprising a location of an epigenetic modification, a time in which the epigenetic modification was collected and a type of epigenetic modification;
- the computer designating a first epigenetic surprisal data at a time point within the time period as a baseline;
- the computer comparing the baseline comprising a location of the epigenetic modification, the time in which the epigenetic modification was collected and the type of epigenetic modification to a next epigenetic surprisal data comprising a location of the epigenetic modification, the time in which the epigenetic modification was collected and the type of epigenetic modification and storing the difference in a repository as epigenetic surprisal data representative of the comparison of the baseline to the next epigenetic surprisal data;
- the computer designating the next epigenetic surprisal data from the comparison as the baseline, and
- the computer repeating the step of comparing and designating, until all epigenetic data in the time period have been compared.

10. The method of claim 9, further comprising a computer recreating an epigenetic map of an organism at a specific time point within the time period by:
- retrieving an epigenetic surprisal data within the time period from the repository;
- retrieving baseline epigenetic surprisal data from the repository; and
- altering the baseline epigenetic surprisal data based on the epigenetic surprisal data at a specific time point by altering the epigenetic map to include epigenetic modifications specified by the epigenetic surprisal data associated with a location; resulting in an entire epigenetic map of an organism at a specific time point within the time period.

11. The method of claim 9, further comprising prior to the computer receiving a request for an epigenetic time series analysis, the computer:
- receiving an epigenetic map at time x of an organism comprising epigenetic modifications;
- comparing the epigenetic map at time x to a reference epigenetic map, to find differences where epigenetic modifications of the organism at time x which are different from the epigenetic modifications of the reference epigenetic map; and
- the computer using the differences to create and store epigenetic surprisal data in a repository.

12. The method of claim 9, wherein the organism is an animal.

13. The method of claim 9, wherein the organism is a microorganism.

14. The method of claim 9, wherein the organism is a plant.

15. The method of claim 9, wherein the organism is a fungus.

16. A computer program product for minimizing epigenetic surprisal data, comprising:
- one or more computer-readable storage mediums;
- program instructions, stored on at least one of the one or more storage mediums, to receive a request for an epigenetic time series analysis comprising at least an indication of a baseline epigenetic surprisal data and a time period for the epigenetic time series analysis;
- program instructions, stored on at least one of the one or more storage mediums, to retrieve a baseline epigenetic surprisal data and epigenetic surprisal data for at least one time point within the time period from a repository;
- program instructions, stored on at least one of the one or more storage mediums, to compare the at least one epigenetic surprisal data comprising a location of the epigenetic modification, the time in which the epigenetic modification was collected and the type of epigenetic modification within the time period to the baseline epigenetic surprisal data comprising a location of the epigenetic modification, the time in which the epigenetic modification was collected and the type of epigenetic modification, producing at least one epigenetic modification difference;
- program instructions, stored on at least one of the one or more storage mediums, to store the at least one epigenetic modification difference in a repository; and
- program instructions, stored on at least one of the one or more storage mediums, to repeat the method for all epigenetic surprisal data time points within the time period.

17. The computer program product of claim 16, further comprising program instructions, stored on at least one of the one or more storage mediums, to recreate an epigenetic map of an organism at a specific time point within the time period by:
- retrieving an epigenetic surprisal data within the time period from the repository;
- retrieving baseline epigenetic surprisal data from the repository; and
- altering the baseline epigenetic surprisal data based on the epigenetic surprisal data at a specific time point by altering the map to include epigenetic modifications specified by the epigenetic surprisal data associated with a location; resulting in an entire epigenetic map of an organism at a specific time point within the time period.

18. The computer program product of claim 16, further comprising prior to the program instructions, stored on at least one of the one or more storage mediums, to receive a request for an epigenetic time series analysis, the computer:
- receiving an epigenetic map at time x of an organism comprising epigenetic modifications;
- comparing the epigenetic map at time x to a reference epigenetic map, to find differences where epigenetic modifications of the organism at time x which are different from the epigenetic modifications of the reference epigenetic map; and
- the computer using the differences to create and store epigenetic surprisal data in a repository.

19. The computer program product of claim 16, wherein the organism is an animal.

20. The computer program product of claim 16, wherein the organism is a microorganism.

21. The computer program product of claim 16, wherein the organism is a plant.

22. The computer program product of claim 16, wherein the organism is a fungus.

23. The computer program product of claim 16, wherein the epigenetic modification is generated by storing only differences between an epigenetic map at time x and a reference epigenetic map.

24. A computer program product for minimizing epigenetic surprisal data, comprising:
- one or more computer-readable, storage mediums;

program instructions, stored on at least one of the one or more storage mediums, to receive a request for an epigenetic time series analysis comprising at least a time period for the epigenetic time series analysis;

program instructions, stored on at least one of the one or more storage mediums, to retrieve epigenetic surprisal data at time points within the time period from a repository;

program instructions, stored on at least one of the one or more storage mediums, to designate a first epigenetic surprisal data at a time point within the time period as a baseline;

program instructions, stored on at least one of the one or more storage mediums, to compare the baseline comprising a location of the epigenetic modification, the time in which the epigenetic modification was collected and the type of epigenetic modification to a next epigenetic surprisal data comprising a location of the epigenetic modification, the time in which the epigenetic modification was collected and the type of epigenetic modification and storing the difference in a repository as epigenetic surprisal data representative of the comparison of the baseline to the next epigenetic surprisal data;

program instructions, stored on at least one of the one or more storage mediums, to designate the next epigenetic surprisal data from the comparison as the baseline, and the program instructions, stored on at least one of the one or more storage mediums, to repeat the step of comparing and designating, until all epigenetic surprisal data in the time period have been compared.

25. The computer program product of claim 24, further comprising program instructions, stored on at least one of the one or more storage mediums, to recreate an epigenetic map of an organism at a specific time point within the time period by:

retrieving an epigenetic surprisal data within the time period from the repository;

retrieving baseline epigenetic surprisal data from the repository; and altering the baseline epigenetic surprisal data based on the epigenetic surprisal data at a specific time point by altering the map to include epigenetic modifications specified by the epigenetic surprisal data associated with a location; resulting in an entire epigenetic map of an organism at a specific time point within the time period.

26. The computer program product of claim 24, further comprising prior to the program instructions, stored on at least one of the one or more storage mediums, to receive a request for an epigenetic time series analysis, the computer:

receiving an epigenetic map at time x of an organism comprising epigenetic modifications;

comparing the epigenetic map at time x to a reference epigenetic map, to find differences where epigenetic modifications of the organism at time x which are different from the epigenetic modifications of the reference epigenetic map; and the computer using the differences to create and store epigenetic surprisal data in a repository.

27. The computer program product of claim 24, wherein the organism is an animal.

28. The computer program product of claim 24, wherein the organism is a microorganism.

29. The computer program product of claim 24, wherein the organism is a plant.

30. The computer program product of claim 24, wherein the organism is a fungus.

31. A computer system for minimizing surprisal data comprising:

one or more processors, one or more computer-readable memories and one or more computer-readable, storage mediums;

program instructions, stored on at least one of the one or more storage mediums for execution by at least one of the one or more processors via at least one of the one or more memories, to receive a request for an epigenetic time series analysis comprising at least an indication of a baseline epigenetic surprisal data and a time period for the epigenetic time series analysis;

program instructions, stored on at least one of the one or more storage mediums for execution by at least one of the one or more processors via at least one of the one or more memories, to retrieve a baseline epigenetic surprisal data and epigenetic surprisal data for at least one time point within the time period from a repository;

program instructions, stored on at least one of the one or more storage mediums for execution by at least one of the one or more processors via at least one of the one or more memories, to compare the at least one epigenetic surprisal data comprising a location of the epigenetic modification, the time in which the epigenetic modification was collected and the type of epigenetic modification within the time period to the baseline epigenetic surprisal data comprising a location of the epigenetic modification, the time in which the epigenetic modification was collected and the type of epigenetic modification, producing at least one epigenetic modification difference;

program instructions, stored on at least one of the one or more storage mediums for execution by at least one of the one or more processors via at least one of the one or more memories, to store the at least one epigenetic modification difference in a repository; and program instructions, stored on at least one of the one or more storage mediums for execution by at least one of the one or more processors via at least one of the one or more memories, to repeat the method for all epigenetic surprisal data time points within the time period.

32. The computer system of claim 31, further comprising program instructions, stored on at least one of the one or more storage mediums for execution by at least one of the one or more processors via at least one of the one or more memories, to recreate an epigenetic map of an organism at a specific time point within the time period by:

retrieving an epigenetic surprisal data within the time period from the repository;

retrieving baseline epigenetic surprisal data from the repository; and altering the baseline epigenetic surprisal data based on the epigenetic surprisal data at a specific time point by altering the map to include epigenetic modifications specified by the epigenetic surprisal data associated with a location; resulting in an entire epigenetic map of an organism at a specific time point within the time period.

33. The computer system of claim 31, further comprising prior to the program instructions, stored on at least one of the one or more storage mediums for execution by at least one of the one or more processors via at least one of the one or more memories, to receive a request for an epigenetic time series analysis, the computer:

receiving an epigenetic map at time x of an organism comprising epigenetic modifications;

comparing the epigenetic map at time x to a reference epigenetic map, to find differences where epigenetic modifications of the organism at time x which are different from the epigenetic modifications of the reference epigenetic map; and the computer using the differences to create and store epigenetic surprisal data in a repository.

34. The computer system of claim 31, wherein the organism is an animal.

35. The computer system of claim 31, wherein the organism is a microorganism.

36. The computer system of claim 31, wherein the organism is a plant.

37. The computer system of claim 31, wherein the organism is a fungus.

38. The computer system of claim 31, wherein the epigenetic modification is generated by storing only differences between an epigenetic map at time x and a reference epigenetic map.

39. A computer system for minimizing epigenetic surprisal data, comprising:
 one or more processors, one or more computer-readable memories and one or more computer-readable, storage mediums;
 program instructions, stored on at least one of the one or more storage mediums for execution by at least one of the one or more processors via at least one of the one or more memories, to a receive a request for an epigenetic time series analysis comprising at least a time period for the epigenetic time series analysis;
 program instructions, stored on at least one of the one or more storage mediums for execution by at least one of the one or more processors via at least one of the one or more memories, to retrieve epigenetic surprisal data at time points within the time period from a repository, the epigenetic surprisal data comprising a location of an epigenetic modification, a time in which the epigenetic modification was collected and a type of epigenetic modification;
 program instructions, stored on at least one of the one or more storage mediums for execution by at least one of the one or more processors via at least one of the one or more memories, to designate a first epigenetic surprisal data at a time point within the time period as a baseline;
 program instructions, stored on at least one of the one or more storage mediums for execution by at least one of the one or more processors via at least one of the one or more memories, to compare the baseline comprising a location of the epigenetic modification, the time in which the epigenetic modification was collected and the type of epigenetic modification to a next epigenetic surprisal data comprising a location of the epigenetic modification, the time in which the epigenetic modification was collected and the type of epigenetic modification and storing the difference in a repository as epigenetic surprisal data representative of the comparison of the baseline to the next epigenetic surprisal data;
 program instructions, stored on at least one of the one or more storage mediums for execution by at least one of the one or more processors via at least one of the one or more memories, to designate the next epigenetic surprisal data from the comparison as the baseline, and
 program instructions, stored on at least one of the one or more storage mediums for execution by at least one of the one or more processors via at least one of the one or more memories, to repeat the step of comparing and designating, until all epigenetic data in the time period have been compared.

40. The computer system of claim 39, further comprising program instructions, stored on at least one of the one or more storage mediums for execution by at least one of the one or more processors via at least one of the one or more memories, to recreate an epigenetic map of an organism at a specific time point within the time period by:
 retrieving an epigenetic surprisal data within the time period from the repository;
 retrieving baseline epigenetic surprisal data from the repository; and
 altering the baseline epigenetic surprisal data based on the epigenetic surprisal data at a specific time point by altering the map to include epigenetic modifications specified by the epigenetic surprisal data associated with a location; resulting in an entire epigenetic map of an organism at a specific time point within the time period.

41. The computer system of claim 39, further comprising prior to the program instructions, stored on at least one of the one or more storage mediums for execution by at least one of the one or more processors via at least one of the one or more memories, to receive a request for an epigenetic time series analysis, the computer:
 receiving an epigenetic map at time x of an organism comprising epigenetic modifications;
 comparing the epigenetic map at time x to a reference epigenetic map, to find differences where epigenetic modifications of the organism at time x which are different from the epigenetic modifications of the reference epigenetic map; and
 the computer using the differences to create and store epigenetic surprisal data in a repository.

42. The computer system of claim 39, wherein the organism is an animal.

43. The computer system of claim 39, wherein the organism is a microorganism.

44. The computer system of claim 39, wherein the organism is a plant.

45. The computer system of claim 39, wherein the organism is a fungus.

\* \* \* \* \*